United States Patent [19]

Braid

[11] 4,194,980

[45] Mar. 25, 1980

[54] SULFURIZED OLEFIN LUBRICANT ADDITIVES AND COMPOSITIONS CONTAINING SAME

[75] Inventor: Milton Braid, Westmont, N.J.

[73] Assignee: Mobil Oil Corporation, New York, N.Y.

[21] Appl. No.: 969,913

[22] Filed: Dec. 15, 1978

[51] Int. Cl.$^2$ .............................................. C10M 1/38
[52] U.S. Cl. .................................. 252/45; 252/78.1; 260/125; 260/139
[58] Field of Search ................ 252/45, 78.1; 260/125, 260/139

[56] References Cited

U.S. PATENT DOCUMENTS

| | | | |
|---|---|---|---|
| 2,708,199 | 5/1955 | Eby | 252/45 X |
| 2,726,236 | 12/1955 | Vaness et al. | 260/139 |
| 3,471,404 | 10/1969 | Myers | 260/139 X |
| 3,697,499 | 10/1972 | Myers | 260/139 |
| 3,703,505 | 11/1972 | Horodysky et al. | 260/139 |
| 3,873,454 | 3/1975 | Horodysky et al. | 252/45 X |
| 3,925,414 | 12/1975 | Landis et al. | 252/45 X |
| 4,132,659 | 1/1979 | Hotten | 260/139 X |

*Primary Examiner*—Andrew Metz
*Attorney, Agent, or Firm*—Charles A. Huggett; Raymond W. Barclay; Howard M. Flournoy

[57] ABSTRACT

Lubricant additives having substantially improved extreme pressure characteristics are provided by modifying certain sulfurized olefins by reacting said olefins with a cyclic polydisulfide under controlled reaction conditions and at a temperature of at least about 130° C.

30 Claims, No Drawings

SULFURIZED OLEFIN LUBRICANT ADDITIVES AND COMPOSITIONS CONTAINING SAME

BACKGROUND OF THE INVENTION

1. Field of the Invention

This invention relates to sulfurized olefins and in particular to modified polysulfurized olefins used in lubricating oil compositions and to a method for preparing the same.

2. Description of the Prior Art

Organic sulfur compounds have been known as additives for lubricating oils. These compounds provide extreme pressure properties to lubricants especially under high speed shock conditions. Unfortunately, the presence of elemental or "hostile" sulfur in lubricating oils often causes considerable corrosion of metals, particularly copper. Since lubricating oils often operate at relatively high temperatures, thermally unstable sulfur compounds may break down resulting in loss of the extreme pressure property and in increased metal corrosion. In U.S. Pat. No. 2,708,199, there is disclosed a method of producing organic polysulfides from olefins having from 6 to 30 carbon atoms resulting in polymers of the olefin containing 2 to 3 sulfur atoms per unsaturated bond of the olefin. However, without proper control of the reaction conditions, the resulting compound may be highly corrosive and unstable. Moreover, if olefins of less than 6 carbon atoms were used in this process, oil insoluble products would be obtained.

SUMMARY OF THE INVENTION

It has now been unexpectedly discovered that novel stable adducts of organosulfur compounds having improved extreme pressure properties are obtained by reacting a sulfurized olefin, as described in U.S. Pat. Nos. 3,471,404, 3,697,499 and 3,703,504 (these patents in their entirety are incorporated herein by reference), and a cyclic polydisulfide as described in U.S. Pat. No. 3,925,414 (which is also incorporated herein in its entirety by reference) under appropriate reaction conditions and at a temperature of about 130° C.

DESCRIPTION OF SPECIFIC EMBODIMENTS

The olefin reactants used to prepare the polysulfurized olefins in this invention may contain from about two to about six carbon atoms. The preferred number of the carbon atoms of the olefin ranges from three to about five. Such olefins as butylene, isobutylene or amylene and isoamylene may be used; in particular, the branched-chain olefins are the most preferred. It has been found that isobutylene has unexpectedly greater reactivity to sulfur chloride than other olefins and yields highly stable reaction products.

In the first step of the novel process herein disclosed, sulfur monochloride or other suitable sulfur halide is reacted with from 1 to 2 moles, preferably from 1.25 to 1.8 moles, of the olefin per mole of the sulfur monochloride. The reaction is carried out by mixing the two reactants at a temperature from 20° C. to about 80° C., preferably 30° to 50° C. The olefin is introduced into the liquid sulfur monochloride subsurface, at a rate commensurate with the absorption rate of the olefin into the sulfur monochloride. This reaction may take from about 1 to 10 hours, although it is preferred that the reaction be carried out as rapidly as possible.

In the second step in the process of this invention the adduct produced in the first step is reacted with an alkali metal sulfide. This may be done in the presence or absence of added free sulfur. That is the adduct may be combined with a mixture of the alkali metal sulfide, preferably sodium sulfide, and sulfur. When sulfur is present the mixture consists of up to about 2.2 moles of the metal sulfide per gram-atom of sulfur and preferably the ratio is 1.8 to 2.2. The mole ratio of alkali metal sulfide to adduct is about 0.8 to about 1.2 moles of metal sulfide per mole of adduct. Ratios within this range are considered significant in determining the oil solubility and thermal stability of the final product. The reaction is usually carried out in the presence of an alcohol or an alcohol-water solvent under reflux conditions. The alcohol may be present in a concentration in the water of from 5 percent to 25 percent by weight. Water-soluble alcohols, such as methanol, ethanol, propanol, isopropanol, butanol, and the like, are preferred. The reflux time ranges from 3 to 6 hours.

The third step in the process of this invention is the reaction between the sulfurized olefin, which contains from about 1 to about 3 percent of residual chlorine, with an inorganic base in a water solution. Alkali metal hydroxide may be used, particularly sodium hydroxide, generally at a concentration of about 5 to about 20 percent and preferably about 8 to 12 percent, by weight in water. The reaction is continued until the chlorine content is below 0.5%. The concentration of the alkali metal hydroxide in water also appears to be important. Higher concentrations may degrade the product severely and lead to reaction products which cannot be separated from the reaction mass easily. The alkali metal hydroxide treatment of the sulfurized olefin is performed under reflux conditions for from about 1 to 24 hours, although a reaction period of 8 hours is usually sufficient. Other inorganic bases which may be used include alkali metal carbonates and ammonia. However, the alkali metal hydroxides, and particularly sodium hydroxide produce the most desirable product with a minimum of process and product complications.

An important feature of these oil-soluble sulfurized olefins is that the products of this invention contain from about 40 to about 60 percent, preferably 42 to 50 percent, of sulfur in stabilized form, and less than 0.5 percent chlorine.

The cyclic polydisulfide reactant is obtained by reacting an olefin, preferably a branched olefin and most preferably isobutylene and a sulfur halide to produce the corresponding adduct; reacting the adduct thus produced with an alkali metal hydrosulfide in a suitable liquid medium to obtain a product comprising a compound in the most preferred form having the structure:

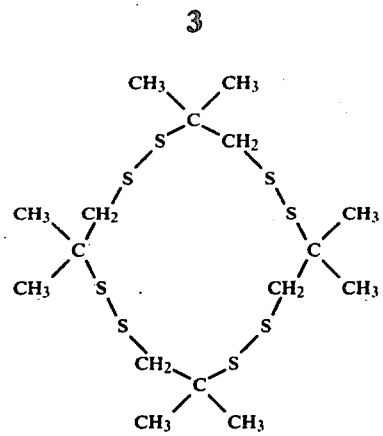

After separating the compound thus produced from the aforesaid reaction mixture, it is found to have a melting point of approximately 254° C. Sufficient alkali metal hydrosulfide is employed to react with all of the adduct. Any alkali metal hydrosulfide may be employed for reaction with the adduct, as hereinbefore described, and may include sodium hydrosulfide, potassium hydrosulfide, lithium hydrosulfide. Any sulfur monohalide may be used for reaction with isobutylene and may include sulfur monochloride, or a combination of a sulfur dihalide and elemental sulfur to produce the corresponding sulfur monohalide which may also be employed as an equivalent reagent. Any suitable liquid medium may be employed for carrying out the reaction between the adduct and the alkali metal hydrosulfide and may include lower alcohols such as methanol, ethanol, propanol and i-propanol.

The cyclic polydisulfide thus produced has a very limited degree of solubility in the sulfurized olefin reactant described above and is even less soluble in the oils of lubricating viscosity used in the formulation of lubricant compositions contemplated in this invention.

These two materials, a sulfurized olefin and a cyclic polydisulfide are then reacted to produce the novel additives in accordance with this invention. The cyclic polydisulfide is thus incorporated into the sulfurized olefin by reaction with the latter under thermal treatment in amounts far exceeding its aforementioned normal solubility in the absence of heating. At the same time, during the thermal treatment, in the presence of the cyclic polydisulfide elemental or "hostile" sulfur which is formed or liberated is reincorporated into the resulting stabilized reaction product. The sulfurized polyolefin may be heated with the cyclic polydisulfide in a reaction mixture in which the cyclic polydisulfide may range from about 2% by weight to about 30% by weight of the mixture. In the preferred practice of this invention, the amount of cyclic polydisulfide is from about 3% to about 20% by weight of the reaction mixture and most preferred is the range from about 8% to about 15% by weight of the mixture. The temperature at which the thermal reaction of sulfurized olefin and cyclic polydisulfide is carried out may range from about 120° C. to about 160° C. The preferred temperatures range from about 130° C. to about 155° C. and most preferred is the range of from about 135° C. to about 145° C.

The time required for the thermal reaction of this invention varies with the sulfurized olefin and the cyclic polydisulfide used and with the reaction temperature and may range from about 1 to about 24 hours with reaction times of 2 to about 20 hours being preferred and reaction periods of 8 to about 18 hours being most preferred.

The following data and examples will serve to illustrate the marked degree of improvement in extreme pressure performance imparted by the novel additives of the present invention to lubricant compositions. It will be understood, however, that it is not intended that the invention be limited to the particular lubricant compositions disclosed nor the particular additives for imparting extreme pressure properties. Various modifications thereof can be employed and will be readily apparent to those skilled in the art.

EXAMPLE 1

Sulfurized isobutylene was prepared by reaction of sulfur monochloride with isobutylene followed by reaction of the resultant adduction product with sodium sulfide as described in U.S. Pat. Nos. 3,697,499, 3,471,404, 3,703,504.

Anal. 46.45% C; 7.30% H; 43.9% S.

EXAMPLE 2

A mixture of sulfurized isobutylene (175 g) prepared by reaction of sulfur monochloride with isobutylene and with subsequent treatment with sodium sulfide as described in Example 1 and 1,1,5,5,9,9,13,13-octamethyl-3,4,7,8,11,12,15,16-octathiacyclohexadecane (25 g—approximate 12.5 wt. %), prepared as in U.S. Pat. No. 3,925,414, was heated under an inert (nitrogen) atmosphere at 130° C. for a total of 16 hr. during which the amount of insoluble solids visibly diminished. Only traces of hydrogen sulfide were detected during the process. The reaction product was filtered to remove unconsumed reactant cyclic polydisulfide (19 g) and the dark amber, clear, moderately viscous oil reaction product was collected as the filtrate.

Anal. 44.84% C; 6.89% H; 44.9% S.

EXAMPLE 3

(Effect of Thermal Treatment in the Absence of the Cyclic Polydisulfide)

Sulfurized isobutylene (197 g) prepared by reaction of sulfur monochloride with isobutylene followed by treatment of the adduct products with sodium sulfide as described in U.S. Pat. No. 3,471,404 and Example 1 was heated at 140°14 144° C. for 4 hr. under an inert (nitrogen) atmosphere. At the end of the reaction period the sulfurized isobutylene had become a dark amber color, but remained clear.

EXAMPLE 4

A sample of sulfurized isobutylene of Example 1 (231.4 g) was heated under a nitrogen atmosphere for four periods of 2 hr. each at 143°-152°, 144°-145°, 141°-143° C., and 141°-143° C., respectively with small test samples of 10-30 g. withdrawn after every heating period for examination. No hydrogen sulfide evolution was detected throughout and weight loss at each heating period exceeded 0.4 g. only once amber oil.

EXAMPLE 5

Prepared in accordance with Example 2 except with 3.1 wt. % of the cyclic polydisulfide at a temperature of from about 145° to 150° C.

Load Carrying (EP) Gear Test

A standard test found in U.S. Federal Standards 791A, sublisted as Test Method 6504.

The test was conducted on a fully formulated gear oil comprising a base oil containing constant fixed weight percent of an additive concentrate. The additive concentrate composition consisted of antirust, anticorrosion, and antifoam agents in addition to the sulfurized olefin extreme pressure additive. The base oil was a typical solvent refined paraffinic mineral oil.

As shown by the data tabulated in the Table, the product of the sulfurized olefin cyclic polydisulfide treatment (16 hours at 130° C.) as in Example 2 improved performance at least 10% over the untreated sample (Example 1). Treatment without the cyclic polydisulfide for a total of 8 hours at elevated temperatures of from 141°-152° C. (Example 4) also resulted in substantially poorer EP performance as did treatment for 4 hours (Example 3) without the cyclic polydisulfide at higher temperatures of (140°-144° C.). In fact the products of Examples 3 and 4 performed far worse than the untreated sample of Example 1 demonstrating that thermal treatment in the absence of the cyclic polydisulfide reactant degrades the performance of the sulfurized olefin. On the other hand, treatment with a much smaller amount of cyclic polydisulfide (Example 5) at a higher temperature (145°-150° C.) gave better results than the untreated sample of Example 1 and much better results than Examples 3 and 4. Thus the Table clearly illustrates the improvement of the additive in accordance with the invention, Example 2, over the untreated material, Example 1. It further illustrates that even though Example 5 (containing 3 wt. % polydisulfide) failed to pass the EP test, it was vastly superior to Examples 1, 3 and 4. This fact illustrates that it is not just thermal treatment which makes the herein embodied improvement in the art possible.

The description and disclosure of the preferred embodiments of this invention are not to be construed as presenting limitations in the following claims.

TABLE
EXTREME PRESSURE/LOAD CARRYING GEAR TEST

| Sulfurized Olefin Additive | Sulfurized Olefin in Additive Concentrate[1] | % Scoring | | | | Rating |
| --- | --- | --- | --- | --- | --- | --- |
| | | Pinion Coast | Pinion Drive | Ring Coast | Ring Drive | |
| Example 1 | 62.43 | 15 | 34 | 13 | 25 | Fail |
| Example 2 | 56.75 | 12 | Trace | 13 | Trace | Pass |
| Example 3 | 56.75 | 65 | 0 | 64 | Trace | Fail |
| Example 4 | 56.75 | 98 | 100 | 96 | 100 | Fail |
| Example 5 | 56.75 | 19 | Trace | 20 | 2 | Fail |

[1]Constant amount of additive concentrate in the formulated test oil.

I claim:

1. A lubricating oil composition or grease prepared therefrom containing a major amount of a lubricating oil and a minor amount sufficient to improve extreme pressure properties thereof of a modified polysulfurized olefin produced by (1) reacting sulfur monochloride with an olefin having from 2 to 6 carbon atoms, reacting the product of that reaction with an alkali metal monosulfide and optionally free sulfur, wherein the ratio of the moles of alkali metal sulfide to the gram-atoms of free sulfur is from about 1.8 to about 2.2:1, and reacting the resulting product with an inorganic base in aqueous solution in an amount and for a time sufficient to reduce the chlorine content below about 0.5 wt. % and (2) thereafter reacting at a temperature of about 130° C. to about 155° C. the thus produced product and a cyclic polydisulfide for a time sufficient and under suitable reaction conditions so as to produce a modified sulfurized olefinic product of improved extreme pressure characteristics.

2. The composition of claim 1 wherein the olefin contains 3 to 5 carbon atoms.

3. The composition of claim 1 wherein the olefin is a branched olefin.

4. The composition of claim 1 wherein the olefin is isobutylene.

5. The composition of claim 1 wherein the mole ratio of olefin to sulfur monochloride is from about 1 to 2:1.

6. The composition of claim 5 wherein the mole ratio of olefin to sulfur monochloride is from about 1.25 to 1.8:1.

7. The composition of claim 1 wherein the polysulfurized olefin contains from about 40% to about 60% by weight of sulfur.

8. The composition of claim 7 wherein the polysulfurized olefin contains from about 42% to about 50% by weight of sulfur.

9. The composition of claim 1 wherein the inorganic base is selected from the group consisting of alkali metal hydroxides, alkali metal carbonates and ammonia.

10. The composition of claim 9 wherein the base is an alkali metal hydroxide.

11. The composition of claim 9 wherein the alkali metal hydroxide is sodium hydroxide.

12. The composition of claim 10 wherein the hydroxide is in a 5% to 20% by weight solution in water.

13. The composition of claim 1 wherein the alkali metal sulfide is sodium sulfide.

14. The composition of claim 1 wherein the mole ratio of alkali metal sulfide to sulfur chloride-olefin product is from about 0.8 to about 1:2.

15. The composition of claim 1 wherein the alkali metal monosulfide and sulfur are reacted with the sulfur monochloride-olefin product in the presence of a water-miscible alcohol.

16. The composition of claim 1 wherein the lubricating oil is a mineral oil.

17. The composition of claim 1 wherein the lubricating oil is a synthetic oil.

18. The composition of claim 1 wherein the cyclic polydisulfide is prepared by reacting a $C_2$-$C_{12}$ olefin and a sulfur monohalide to produce an adduct; reacting the adduct thus produced with an alkali metal hydrosulfide in a suitable liquid medium to produce a product containing said cyclic polydisulfide.

19. The composition of claim 18 wherein the reaction to produce the cyclic polydisulfide is conducted at a temperature of from about 0° to 150° C.

20. The composition of claim 18 wherein in said reaction to produce the cyclic polydisulfide, the olefin and the sulfur monohalide are reacted in a mole ratio of from about 0.5:1 to about 2.5:1.

21. The composition of claim 18 wherein in said reaction to produce the cyclic polydisulfide, the adduct and the alkali metal hydrosulfide are reacted in a mole ratio of from about 1:1 to about 1:5.

22. The composition of claim 18 wherein in said reaction to produce the cyclic polydisulfide, the sulfur monohalide is a sulfur monochloride.

23. The composition of claim 18 wherein in said reaction to produce the cyclic polydisulfide, the alkali metal hydrosulfide is sodium hydrosulfide.

24. The composition of claim 18 wherein in said reaction to produce the cyclic polydisulfide, the liquid medium is a lower alcohol.

25. The composition of claim 18 wherein in said reaction to produce the cyclic polydisulfide, the liquid medium is ethyl alcohol.

26. The composition of claim 1 wherein said cyclic polydisulfide is 1,1,5,5,9,9,13,13-octamethyl-3,4,7,8,11,12,15,16-octathiacyclohexadecane.

27. A polysulfurized olefin produced by the steps of (1) reacting sulfur monochloride with from 1 to 2 moles of a $C_2$–$C_{12}$ olefin per mole of said sulfur monohalide at a temperature of from 20° C. to about 80° C., (2) reacting the product thereof with an alkali metal monosulfide and optionally free sulfur, wherein the ratio of the moles of alkali metal monosulfide to the gram-atoms of free sulfur is from about 1.8 to about 2.2:1 and (3) reacting this product with an aqueous solution containing from about 5 to about 20 wt. percent of an alkali metal hydroxide for a time sufficient to reduce the chlorine content below about 0.5 wt. percent, (4) reacting at a temperature of about 130° C. the thus produced sulfurized product and a cyclic polydisulfide.

28. The polysulfurized olefin of claim 27 wherein the $C_2$–$C_{12}$ olefin is isobutylene, the sulfur monohalide is sulfur monochloride, the alkali metal sulfide is sodium sulfide.

29. The polysulfurized olefin of claim 27 wherein said polysulfurized olefin contains from about 40 to 60 percent of sulfur.

30. The polysulfurized olefin of claim 27 wherein the cyclic polydisulfide is 1,1,5,5,9,19,13,13,-octamethyl-3,4,7,8,11,12,15,16-octathiacyclohexadecane.

* * * * *

UNITED STATES PATENT AND TRADEMARK OFFICE
CERTIFICATE OF CORRECTION

PATENT NO. : 4,194,980
DATED : March 25, 1980
INVENTOR(S) : MILTON BRAID

It is certified that error appears in the above-identified patent and that said Letters Patent are hereby corrected as shown below:

Column 4, line 49, "at 140° 14 144°C" should read --at 140°-144°C--.

Column 4, line 64, "only once amber oil." should read --only once (at 0.89). The final product, 184 g. was a dark clear amber oil.--

Column 8, line 21, "polysulfide is 1,1,5,5,9,19,13,13" should read --polysulfide is 1,1,5,5,9,9,13,13 --.

Signed and Sealed this

Twelfth Day of August 1980

[SEAL]

Attest:

SIDNEY A. DIAMOND

Attesting Officer

Commissioner of Patents and Trademarks